(12) United States Patent
Kallenberger

(10) Patent No.: US 11,439,474 B2
(45) Date of Patent: Sep. 13, 2022

(54) SURGICAL TOOLS WITH OPPOSING TRANSLATING GEARS

(71) Applicant: Ethicon LLC, Guaynabo, PR (US)

(72) Inventor: Kris Eren Kallenberger, Cincinnati, OH (US)

(73) Assignee: CILAG GMBH INTERNATIONAL, Zug (CH)

(*) Notice: Subject to any disclaimer, the term of this patent is extended or adjusted under 35 U.S.C. 154(b) by 954 days.

(21) Appl. No.: 16/170,485

(22) Filed: Oct. 25, 2018

(65) Prior Publication Data

US 2020/0129255 A1 Apr. 30, 2020

(51) Int. Cl.
*A61B 34/00* (2016.01)
*A61B 18/00* (2006.01)
(Continued)

(52) U.S. Cl.
CPC .............. *A61B 34/71* (2016.02); *A61B 10/00* (2013.01); *A61B 17/00* (2013.01);
(Continued)

(58) Field of Classification Search
CPC ... A61B 34/71; A61B 17/00234; A61B 10/00; A61B 17/00; A61B 18/00; A61B 2018/00208; A61B 17/320758; A61B 2017/00017; A61B 2034/302; A61B 2034/305; A61B 2034/306; A61B 34/70; A61B 34/35
See application file for complete search history.

(56) References Cited

U.S. PATENT DOCUMENTS

| 9,220,569 B2 | 12/2015 | Parihar et al. |
| 2014/0001231 A1* | 1/2014 | Shelton, IV ........... A61B 34/71 227/175.3 |

(Continued)

FOREIGN PATENT DOCUMENTS

| WO | 2016064616 A1 | 4/2016 | |
| WO | 2017037723 A1 | 3/2017 | |
| WO | WO-2017037723 A1 * | 3/2017 | .............. B25J 9/102 |

OTHER PUBLICATIONS

ISR-WO from PCT/IB2019/057817, which claims priority to the present application, dated Dec. 10, 2019.

*Primary Examiner* — Gary Jackson
*Assistant Examiner* — Sebastian X Lukjan
(74) *Attorney, Agent, or Firm* — Vorys, Sater, Seymour and Pease LLP

(57) ABSTRACT

A surgical tool includes a drive housing having a shaft extending distally therefrom, first and second drive members extending distally from the drive housing along the shaft, and first and second translating gears rotationally fixed to the shaft within the drive housing and operatively coupled to the first and second drive members, respectively. First and second drive gears are rotatably mounted within the drive housing to act on the first and second translating gears, respectively. Rotating the first and second drive gears in opposite angular directions causes the first and second translating gears to move axially along the shaft in opposing directions and thereby move the first and second drive members. Rotating the first and second drive gears in a same angular direction causes the first and second translating gears to rotate the shaft about a longitudinal axis.

19 Claims, 5 Drawing Sheets

(51) Int. Cl.
*A61B 10/00* (2006.01)
*A61B 17/00* (2006.01)
*A61B 34/30* (2016.01)
*A61B 17/3207* (2006.01)

(52) U.S. Cl.
CPC ........ *A61B 17/00234* (2013.01); *A61B 18/00* (2013.01); *A61B 17/320758* (2013.01); *A61B 2017/00017* (2013.01); *A61B 2018/00208* (2013.01); *A61B 2034/302* (2016.02); *A61B 2034/305* (2016.02)

(56) References Cited

U.S. PATENT DOCUMENTS

| | | |
|---|---|---|
| 2015/0038981 A1 | 2/2015 | Kilroy et al. |
| 2015/0164540 A1* | 6/2015 | Higgins ......... A61B 17/320758 606/159 |
| 2015/0214816 A1* | 7/2015 | Raad .................... H02K 7/1807 310/54 |
| 2017/0135776 A1 | 5/2017 | Cohen et al. |

* cited by examiner

SURGICAL TOOLS WITH OPPOSING TRANSLATING GEARS

BACKGROUND

Minimally invasive surgical (MIS) instruments or tools are often preferred over traditional open surgical devices due to reduced post-operative recovery time and minimal scarring. Laparoscopic surgery is one type of MIS procedure in which one or more small incisions are formed in the abdomen of a patient and a trocar is inserted through the incision to form a pathway that provides access to the abdominal cavity. Through the trocar, a variety of instruments and surgical tools can be introduced into the abdominal cavity. The instruments and tools introduced into the abdominal cavity via the trocar can be used to engage and/or treat tissue in a number of ways to achieve a diagnostic or therapeutic effect.

Various robotic systems have recently been developed to assist in MIS procedures. Robotic systems can allow for more intuitive hand movements by maintaining natural eye-hand axis. Robotic systems can also allow for more degrees of freedom in movement by including an articulable "wrist" joint that creates a more natural hand-like articulation. In such systems, an end effector positioned at the distal end of the tool can be articulated (moved) using a member driven motion system having one or more drive members that extend to and/or through the wrist joint. A user (e.g., a surgeon) is able to remotely operate the end effector by grasping and manipulating in space one or more controllers that communicate with a tool driver coupled to the surgical tool. User inputs are processed by a computer system incorporated into the robotic surgical system, and the tool driver responds by actuating the member driven motion system.

Selectively moving the drive members will articulate the end effector to desired angular positions and configurations, and may also cause the end effector to actuate (e.g., open, close, cut, staple, etc.). In robotic surgical tools, a plurality of actuators or mechanisms are arranged within a drive housing and configured to move the drive members as actuated through operation of the interconnected tool driver. Improvements to the design of such devices are desirable to reduce the footprint within the drive housing and provide consistent and predictable performance of the end effector.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

DETAILED DESCRIPTION

The present disclosure is related to surgical systems and, more particularly, to surgical tools having improved member driven motion systems.

Embodiments discussed herein describe drive member articulation systems that may use only two drive inputs to cause articulation of an articulable joint and rotation of a shaft. One example surgical tool includes a drive housing having a shaft extending distally therefrom. First and second drive members extend distally from the drive housing along the shaft, and first and second translating gears may be rotationally fixed to the shaft within the drive housing. The translating gears may be operatively coupled to the first and second drive members, respectively, such that axial movement of the translating gears correspondingly moves the associated drive member. First and second drive gears may be rotatably mounted within the drive housing to act on the first and second translating gears, respectively. In example operation, rotating the first and second drive gears in opposite angular directions may cause the first and second translating gears to move axially along the shaft in opposing directions and thereby move the first and second drive members. Moreover, rotating the first and second drive gears in a same angular direction may cause the first and second translating gears to rotate the shaft about a longitudinal axis.

Figure 1:
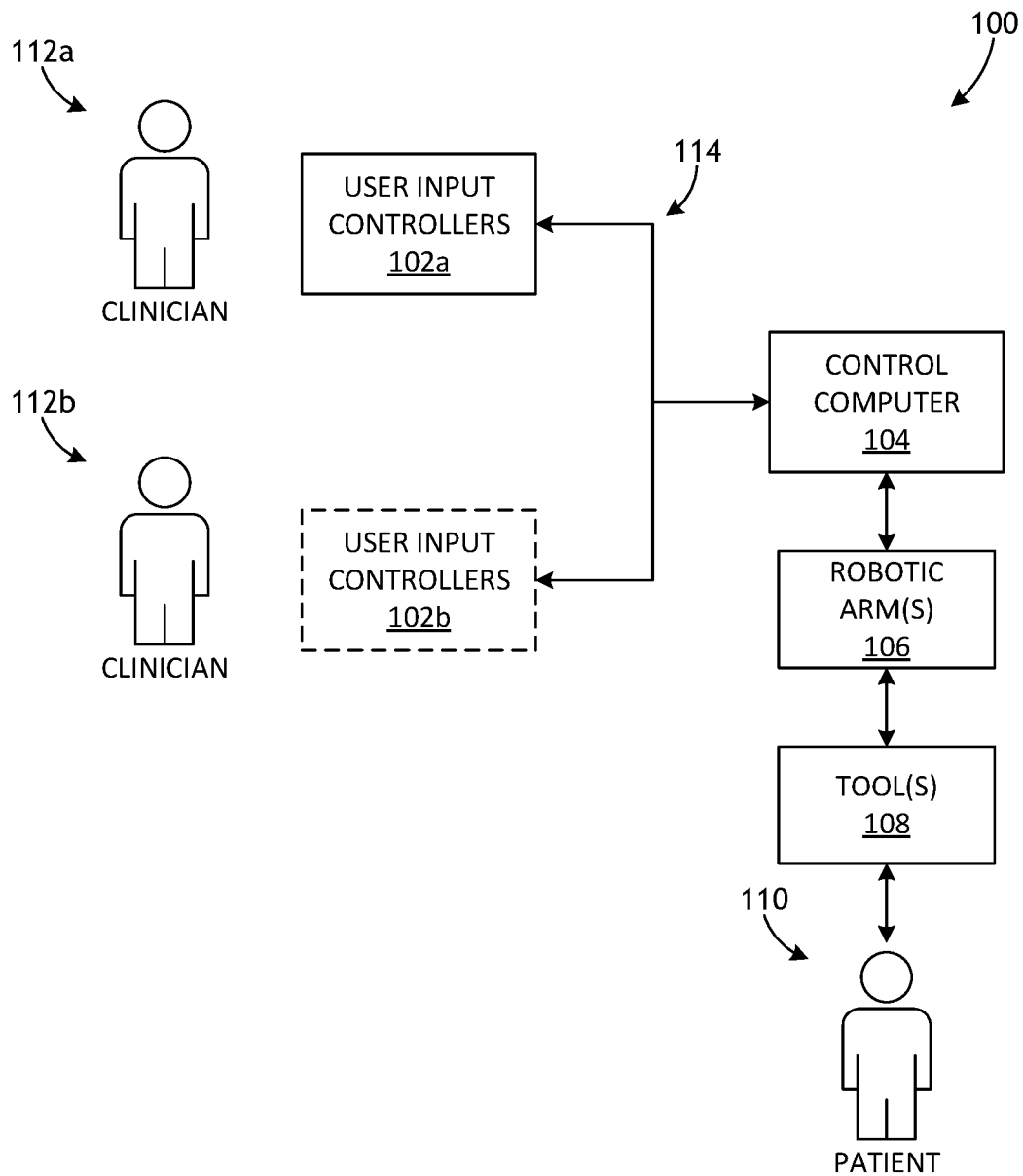
FIG. 1 is a block diagram of an example robotic surgical system that may incorporate some or all of the principles of the present disclosure.

FIG. 1 is a block diagram of an example robotic surgical system 100 that may incorporate some or all of the principles of the present disclosure. As illustrated, the system 100 can include at least one set of user input controllers 102a and at least one control computer 104. The control computer 104 may be mechanically and/or electrically coupled to a robotic manipulator and, more particularly, to one or more robotic arms 106 (alternately referred to as "tool drivers"). In some embodiments, the robotic manipulator may be included in or otherwise mounted to an arm cart capable of making the system portable. Each robotic arm 106 may include and otherwise provide a location for mounting one or more surgical instruments or tools 108 for performing various surgical tasks on a patient 110. Operation of the robotic arms 106 and associated tools 108 may be directed by a clinician 112a (e.g., a surgeon) from the user input controller 102a.

In some embodiments, a second set of user input controllers 102b (shown in dashed lines) may be operated by a second clinician 112b to direct operation of the robotic arms 106 and tools 108 in conjunction with the first clinician 112a. In such embodiments, for example, each clinician 112a,b may control different robotic arms 106 or, in some cases, complete control of the robotic arms 106 may be passed between the clinicians 112a,b. In some embodiments, additional robotic manipulators (not shown) having additional robotic arms (not shown) may be utilized during surgery on the patient 110, and these additional robotic arms may be controlled by one or more of the user input controllers 102a,b.

The control computer 104 and the user input controllers 102a,b may be in communication with one another via a communications link 114, which may be any type of wired or wireless telecommunications means configured to carry a variety of communication signals (e.g., electrical, optical, infrared, etc.) according to any communications protocol. In some applications, for example, there is a tower with ancillary equipment and processing cores designed to drive the robotic arms 106.

The user input controllers 102a,b generally include one or more physical controllers that can be grasped by the clinicians 112a,b and manipulated in space while the surgeon views the procedure via a stereo display. The physical controllers generally comprise manual input devices movable in multiple degrees of freedom, and which often include an actuatable handle for actuating the surgical tool(s) 108, for example, for opening and closing opposing jaws, applying an electrical potential (current) to an electrode, or the like. The control computer 104 can also include an optional feedback meter viewable by the clinicians 112a,b via a display to provide a visual indication of various surgical instrument metrics, such as the amount of force being applied to the surgical instrument (i.e., a cutting instrument or dynamic clamping member).

Figure 2:
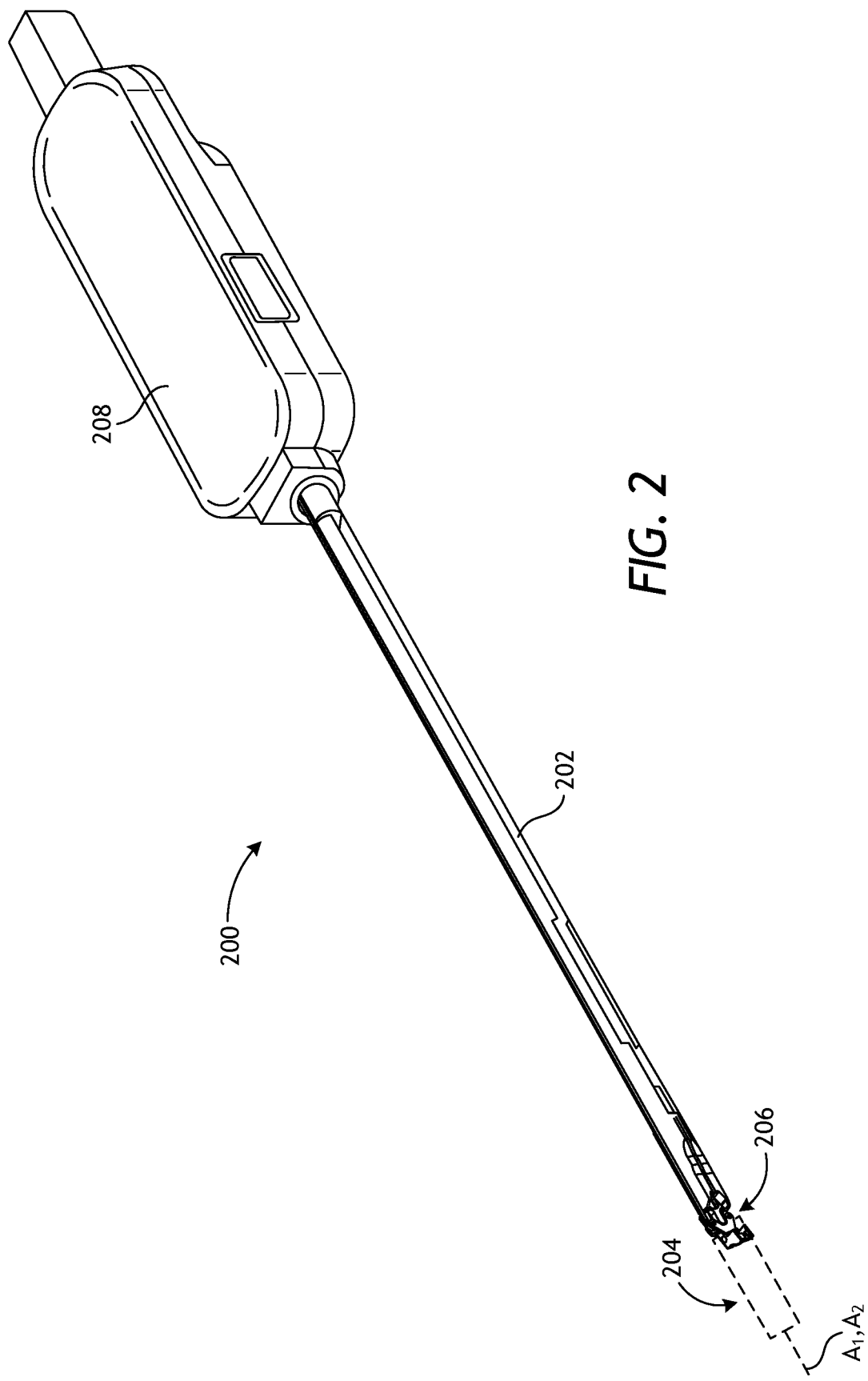
FIG. 2 is an isometric side view of an example surgical tool that may incorporate some or all of the principles of the present disclosure.

FIG. 2 is an isometric side view of an example surgical tool 200 that may incorporate some or all of the principles of the present disclosure. The surgical tool 200 may be the same as or similar to the surgical tool(s) 108 of FIG. 1 and, therefore, may be used in conjunction with a robotic surgical system, such as the robotic surgical system 100 of FIG. 1. Accordingly, the surgical tool 200 may be designed to be releasably coupled to a tool driver included in the robotic surgical system 100.

As illustrated, the surgical tool 200 includes an elongated shaft 202, an end effector 204 (shown in dashed lines), an articulable joint 206 (alternately referred to as a "wrist joint") that couples the end effector 204 to the distal end of the shaft 202, and a drive housing 208 coupled to the proximal end of the shaft 202. In applications where the surgical tool 200 is used in conjunction with a robotic surgical system (e.g., the robotic surgical system 100 of FIG. 1), the drive housing 208 can include coupling features that releasably couple the surgical tool 200 to the robotic surgical system and, more particularly, to a tool driver. As indicated above, however, the principles of the present disclosure are equally applicable to surgical tools that are non-robotic and otherwise capable of manual manipulation.

The terms "proximal" and "distal" are defined herein relative to a robotic surgical system having an interface configured to mechanically and electrically couple the surgical tool 200 (e.g., the housing 208) to a robotic manipulator. The term "proximal" refers to the position of an element closer to the robotic manipulator and the term "distal" refers to the position of an element closer to the end effector 204 and thus further away from the robotic manipulator. Moreover, the use of directional terms such as above, below, upper, lower, upward, downward, left, right, and the like are used in relation to the illustrative embodiments as they are depicted in the figures, the upward or upper direction being toward the top of the corresponding figure and the downward or lower direction being toward the bottom of the corresponding figure.

During use of the surgical tool 200, the end effector 204 is configured to articulate (pivot) relative to the shaft 202 at the articulable joint 206 to position the end effector 204 at desired orientations and locations relative to a surgical site. The housing 208 includes (contains) various mechanisms designed to control articulation of the end effector 204 and operation of various features associated with the end effector 204 (e.g., clamping, firing, rotation, articulation, energy delivery, etc.). In at least some embodiments, the shaft 202 (and hence the end effector 204 coupled thereto) is configured to rotate about a longitudinal axis $A_1$ of the shaft 202.

In such embodiments, at least one of the mechanisms included (housed) in the housing 208 is configured to control rotational movement of the shaft 202 about the longitudinal axis $A_1$.

The surgical tool 200 can have any of a variety of configurations capable of performing at least one surgical function, and the end effector 204 can have a variety of sizes, shapes, and configurations. For example, the end effector 204 may comprise, but is not limited to, forceps, a grasper, a needle driver, scissors, an electro cautery tool, a stapler, a clip applier, a suction tool, an irrigation tool, an imaging device (e.g., an endoscope or ultrasonic probe), or any combination thereof. In some embodiments, the end effector 204 may include opposing jaws configured to pivot between open and closed positions. In such embodiments, the end effector 204 can comprise, but is not limited to, a tissue grasper, a clip applier, scissors, a needle driver, a babcock including a pair of opposed grasping jaws, etc. Moreover, in such embodiments, one or both of the jaws may be configured to pivot at the articulable joint 206 to articulate the end effector 204 between the open and closed positions. In one or more embodiments, the surgical tool 200 may further be configured to apply energy (e.g., radiofrequency energy) to tissue via the end effector 204.

The shaft 202 is an elongate member extending distally from the housing 208 and has at least one lumen extending therethrough along its axial length. In some embodiments, the shaft 202 may be fixed to the housing 208, but could alternatively be rotatably mounted to the housing 208 to allow the shaft 202 to rotate about the longitudinal axis $A_1$. In yet other embodiments, the shaft 202 may be releasably coupled to the housing 208, which may allow a single housing 208 to be adaptable to various shafts having different end effectors.

The surgical tool 200 includes a plurality of drive members (obscured in FIG. 2) that form part of a member driven motion system configured to facilitate movement (articulation) of the end effector 204 relative to the shaft 202. Moving the drive members moves the end effector 204 between an unarticulated position and an articulated position. The end effector 204 is depicted in FIG. 2 in the unarticulated position where a longitudinal axis $A_2$ of the end effector 204 is substantially aligned with the longitudinal axis $A_1$ of the shaft 202, such that the end effector 204 is at a substantially zero angle relative to the shaft 202. Due to factors such as manufacturing tolerance and precision of measurement devices, the end effector 204 may not be at a precise zero angle relative to the shaft 202 in the unarticulated position, but nevertheless be considered "substantially aligned" thereto. In the articulated position, the longitudinal axes $A_1$, $A_2$ would be angularly offset from each other such that the end effector 204 is at a non-zero angle relative to the shaft 202.

Figure 3:
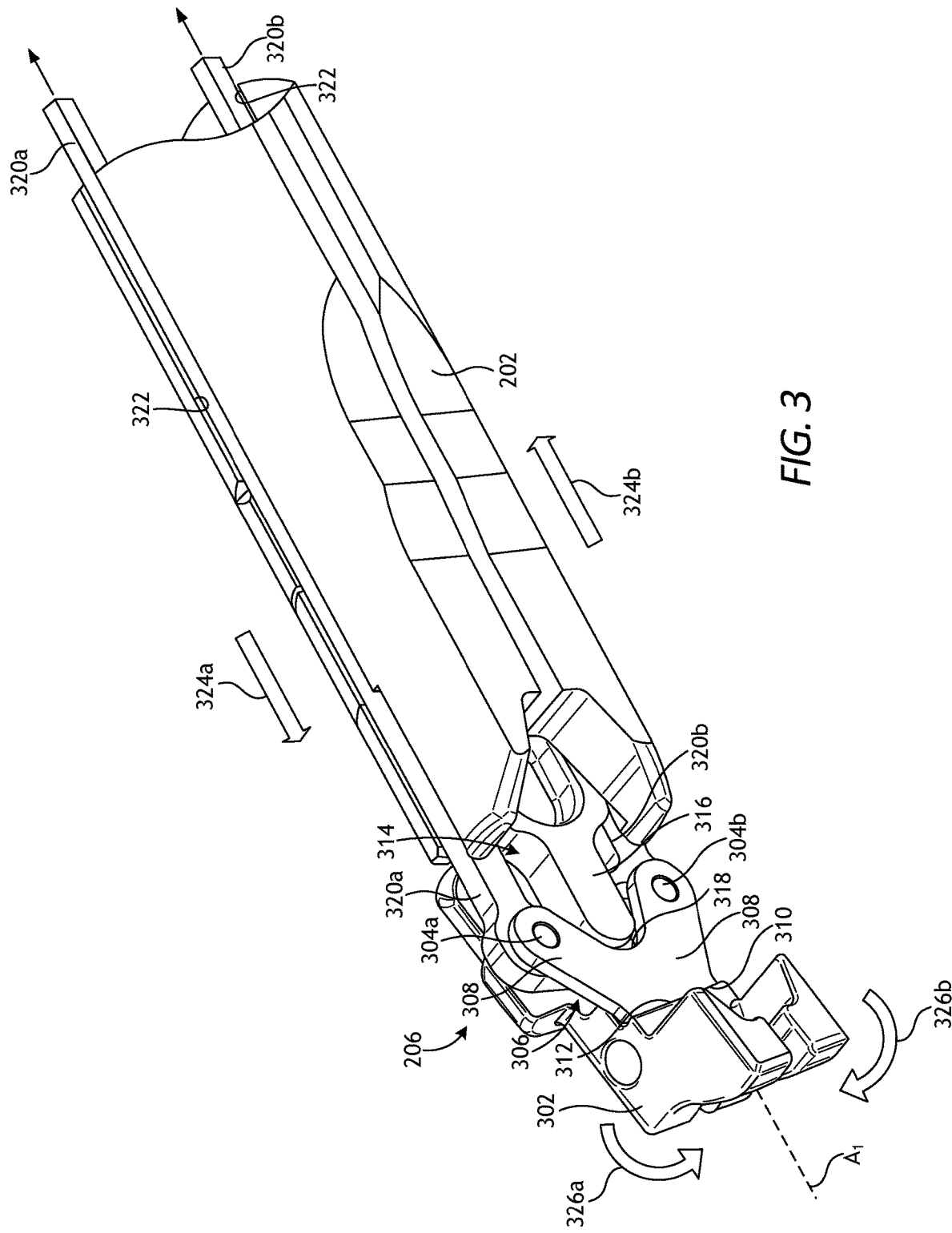
FIG. 3 is an enlarged isometric view of the distal end of the surgical tool of FIG. 2.

FIG. 3 is an enlarged isometric view of the distal end of the surgical tool 200 of FIG. 2. More specifically, FIG. 3 depicts an enlarged view of the articulable joint 206, which operatively couples the shaft 202 to an end effector (e.g., the end effector 204 of FIG. 2). As used herein, the term "operatively couple," or any variation thereof, refers to a direct or indirect coupling engagement between two component parts. The articulable joint 206 described herein below is in accordance with one example embodiment. However, those skilled in the art will readily appreciate that several variations of the articulable joint 206 may be employed, without departing from the scope of the disclosure. Accordingly, the description of the articulable joint 206 is provided herein merely for illustrative purposes and should not be considered limiting to the present disclosure.

The articulable joint 206 includes a distal channel retainer 302 that provides a location where the end effector can be operatively coupled (mounted) to the articulable joint 206. In the illustrated embodiment, the distal channel retainer 302 provides or otherwise defines a first articulation pin 304a and a second articulation pin 304b. The articulation pins 304a,b may be used to articulate, or restrain from articulating, the distal channel retainer 302 and, consequently, the end effector that may be mounted thereto.

The articulable joint 206 may further include a retainer plate 306. In the illustrated embodiment, the retainer plate 306 provides or otherwise defines opposing legs 308 that may be secured to the first and second articulation pins 304a,b. The retainer plate 306 may further include or define a biasing surface 310 engageable with a shoulder 312 provided on the distal channel retainer 302. Securing the legs 308 to the articulation pins 304a,b and simultaneously engaging the biasing surface 310 against the shoulder 312 may effectively couple the retainer plate 306 to the distal channel retainer 302 such that movement (rotation) of the distal channel retainer 302 correspondingly moves (rotates) the retainer plate 306 in the same direction. While the retainer plate 306 and the distal channel retainer 302 are depicted as separate component parts, in at least one embodiment, the retainer plate 306 may alternatively form an integral part or extension of the distal channel retainer 302, without departing from the scope of the disclosure.

The articulable joint 206 may further include an articulation connector 314 mounted to or otherwise coupled to the shaft 202 at or near its distal end. As illustrated, the articulation connector 314 may include an extension 316 receivable within a saddle 318 defined between the legs 308 of the retainer plate 306. The articulation connector 314 may contain a pivoting pin that mates to a matching hole in the distal channel retainer 302. While the articulation connector 314 and the shaft 202 are depicted as separate component parts, in at least one embodiment, the articulation connector 314 may alternatively form an integral part or extension of the shaft 202, without departing from the scope of the disclosure.

One or more drive members (alternately referred to as "articulation bands"), shown as a first drive member 320a and a second drive member 320b, may extend longitudinally along the shaft 202 and terminate at the articulable joint 206. In at least one embodiment, as illustrated, the drive members 320a,b may be positioned within corresponding slots 322 defined longitudinally along all or a portion of the shaft 202. In other embodiments, however, the drive members 320a,b may extend wholly or partially within the interior of the shaft 202, without departing from the scope of the disclosure.

In the illustrated embodiment, the drive members 320a,b comprise rigid or semi-rigid elongate members such as, but not limited to, rods, shafts, tubes, or bands that may be pushed and pulled axially to articulate the articulable joint 206. In other embodiments, however, one or more of the drive members 320a,b may comprise flexible or non-rigid elongate members such as, but not limited to, a cable, a line, a cord, a wire, a rope, a string, a twisted string, or any combination thereof, without departing from the scope of the disclosure. The drive members 320a,b can be made from a variety of materials including, but not limited to, metal (e.g., tungsten, stainless steel, etc.), a polymer, a composite material, or any combination thereof.

The drive members 320a,b form part of the member driven motion system briefly mentioned above. In the illustrated embodiment, the distal ends of the drive members 320a,b are pivotably coupled to the first and second articulation pins 304a,b, respectively. As described below, the proximal ends of the drive members 320a,b extend proximally to the drive housing 208 (FIG. 2) where they may be operatively coupled to various actuation mechanisms or devices housed (contained) therein. While not shown, one or more additional drive members may be included in the surgical tool 200 (FIG. 2) and extend to or through the articulable joint 206. In some embodiments, the additional drive members may terminate at the articulable joint 206 and help articulate the articulable joint 206 in multi-plane articulation. In other embodiments, or in addition thereto, the additional drive members may be operatively coupled to the end effector mounted to the distal channel retainer 302 and selectively actuated to operate the end effector in accordance with its design.

Selective actuation of one or both of the drive members 320a,b may cause the articulable joint 206 to articulate (pivot) relative to the shaft 202. In example operation, movement of the first drive member 320a in the distal direction 324a and simultaneous movement of the second drive member 320b in the proximal direction 324b may cause the distal channel retainer 302 to rotate (pivot) in a first direction 326a relative to the longitudinal axis $A_1$ of the shaft 202. As the first drive member 320a pushes distally 322a against the first articulation pin 304a, and the second drive member 320b pulls proximally 322b on the second articulation pin 304b, the retainer plate 306 (and the distal channel retainer 302) will correspondingly pivot about the extension 316 in the first direction 326a. In contrast, movement of the first drive member 320a in the proximal direction 324b and simultaneous movement of the second drive member 320b in the distal direction 324a may cause the distal channel retainer 302 to rotate (pivot) in a second direction 326b relative to the longitudinal axis $A_1$. As the first drive member 320a pulls proximally 322b on the first articulation pin 304a, and the second drive member 320b pushes distally 322a against the second articulation pin 304b, the retainer plate 306 (and the distal channel retainer 302) will pivot about the extension 316 in the second direction 326b.

In the illustrated embodiment, the drive members 320 may be configured to slide longitudinally within the slots 322 as they are translated distally 324a and proximally 324b. The slots 322 may help prevent the drive members 320a,b from buckling during loading when being pushed in the distal direction 324a. However, as noted above, one or both of the drive members 320a,b may alternatively comprise a cable, a line, a cord, a wire, etc. that may be largely unable to be pushed. In such embodiments, the second drive member 320b may be pulled proximally 324b to cause the distal channel retainer 302 to rotate (pivot) in the first direction 326a, and the first drive member 320a may be pulled proximally 324b to cause the distal channel retainer 302 to rotate (pivot) in the second direction 326b.

Accordingly, the articulable wrist 206 in the illustrated embodiment is configured for single plane articulation, where the distal channel retainer 302 (and consequently an end effector mounted thereto) is capable of pivoting in the first and second directions 326a,b in the same plane. It is noted, however, that the principles of the present disclosure are equally applicable to applications that include an articulable wrist providing multi-plane plane articulation. In such embodiments, additional drive members be provided at the articulable joint 206 to help facilitate multi-plane articulation.

Figure 4:
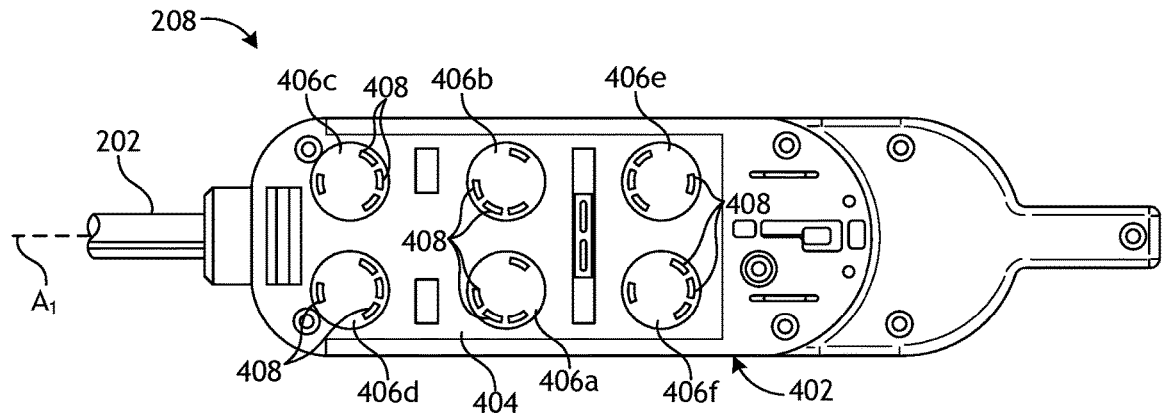
FIG. 4 is a bottom view of the drive housing of FIG. 2, according to one or more embodiments.

FIG. 4 is a bottom view of the drive housing 208, according to one or more embodiments. As illustrated, the drive housing 208 (alternately referred to as a "puck") may include a tool mounting portion 402 used to operatively couple the drive housing 208 to a tool driver of a robotic manipulator. The tool mounting portion 402 may releasably couple the drive housing 208 to a tool driver in a variety of ways, such as by clamping thereto, clipping thereto, or slidably mating therewith. In some embodiments, the tool mounting portion 402 may include an array of electrical connecting pins or connection points, which may be coupled to an electrical connection on the mounting surface of the tool driver. While the tool mounting portion 402 is described herein with reference to mechanical, electrical, and magnetic coupling elements, it should be understood that a wide variety of telemetry modalities might be used, including infrared, inductive coupling, etc.

The tool mounting portion 402 includes and otherwise provides an interface 404 configured to mechanically, magnetically, and/or electrically couple the drive housing 208 to a tool driver. As illustrated, the interface 404 includes and supports a plurality of inputs, shown as drive inputs 406a, 406b, 406c, 406d, 406e, and 406f. In at least one embodiment, each drive input 406a-f comprises a rotatable disc configured to align with and couple to a corresponding actuator of the tool driver. Moreover, each drive input 406a-f provides or defines one or more surface features 408 configured to align with mating surface features provided on the corresponding actuator. The surface features 408 can include, for example, various protrusions and/or indentations that facilitate a mating engagement. Each of the drive inputs 406a-f may be actuated based on user inputs communicated to the tool driver coupled to the interface 404, and the user inputs may be received via a computer system incorporated into the robotic surgical system.

In some embodiments, actuation of the first drive input 406a may control movement (axial translation) of the first drive member 320a (FIG. 3), and actuation of the second drive input 406b may control movement (axial translation) of the second drive member 320b (FIG. 3). Moreover, as described in more detail below, simultaneous actuation of the first and second drive inputs 406a,b in the same angular direction may control rotation of the shaft 202 about its longitudinal axis $A_1$. The shaft 202 may be rotated clockwise or counter-clockwise depending on the simultaneous rotational actuation of the first and second drive inputs 406a,b.

Actuation of the third, fourth, fifth, and sixth drive inputs 406c-f may cause actuation or operation of other features of the surgical tool 200 (FIG. 2). For example, actuation of one or more of the third, fourth, fifth, and sixth drive inputs 406c-f may control movement (axial translation) of additional drive members to help articulate the end effector 204 (FIG. 2) in multi-plane articulation, as briefly mentioned above. In other embodiments, actuation of one or more of the third, fourth, fifth, and sixth drive inputs 406c-f may control operation of the end effector 204 (e.g., clamping, firing, rotation, articulation, energy delivery, etc.). In yet other embodiments, actuation of one or more of the third, fourth, fifth, and sixth drive inputs 406c-f may be configured to control a lockout mechanism, which locks the end effector 204 in a predetermined pose or position.

Figure 5:
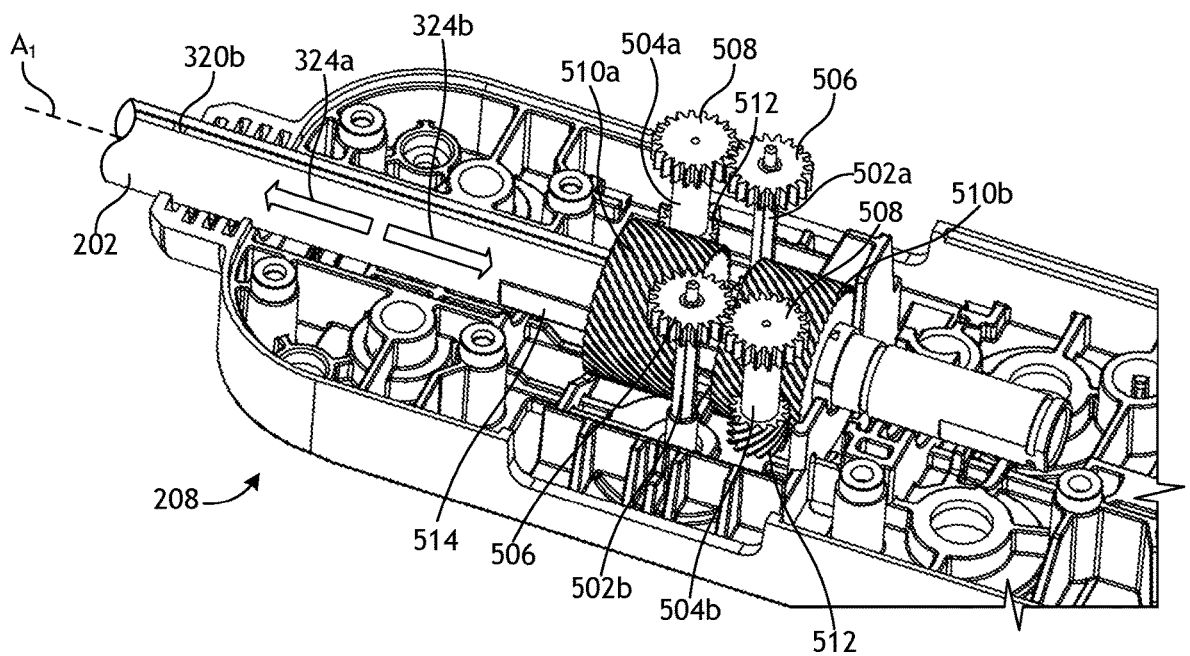
FIG. 5 is an isometric exposed view of the interior of the drive housing of FIG. 4, according to one or more embodiments.

FIG. 5 is an isometric exposed view of the interior of the drive housing 208, according to one or more embodiments. Several component parts that would otherwise be included within the drive housing 208 are omitted in FIG. 5 to simplify the figure and enable discussion of the depicted component parts. As illustrated, a first capstan 502a and a second capstan 502b are rotatably mounted within the drive housing 208. The first capstan 502a may be operatively coupled to or extend from the first drive input 406a (FIG. 4), and the second capstan 502b may be operatively coupled to or extend from the second drive input 406b (FIG. 4). Accordingly, actuation of the first and second drive inputs 406a results in rotation of the first and second capstans 502a,b respectively.

A first drive shaft 504a and a second drive shaft 504b may also be rotatably mounted within the drive housing 208. In the illustrated embodiment, each capstan 502a,b has a capstan drive gear 506 coupled thereto or forming part thereof, and each capstan drive gear 506 is positioned to mesh and interact with a corresponding driven gear 508 coupled to or forming part of each drive shaft 504a,b. In some embodiments, the drive and driven gears 506, 508 may comprise mating spur gears. Accordingly, rotation of the first capstan 502a (via actuation of the first drive input 406a of FIG. 4) will control rotation of the first drive shaft 504a via the corresponding intermeshed drive and driven gears, 506, 508. Similarly, rotation of the second capstan 502b (via actuation of the second drive input 406b of FIG. 4) will control rotation of the second drive shaft 504b via the corresponding intermeshed drive and driven gears, 506, 508.

The drive housing 208 may further contain or house a first or "distal" translating gear 510a and a second or "proximal" translating gear 510b, and each translating gear 510a,b may be mounted to and otherwise extend about the outer circumference of the shaft 202. Corresponding drive gears 512 may be positioned within the drive housing 208 to mesh and act on the associated translating gear 510a,b. Rotation of the first and second capstans 502a,b will cause the corresponding drive gears 512 to act on the first and second translating gears 510a,b, respectively. In the illustrated embodiment, the first and second translating gears 510a,b and the associated drive gears 512 are depicted as helical driven and drive gears, respectively. In other embodiments, however, the first and second translating gears 510a,b and the associated drive gears 512 may comprise other types or designs of driven and drive gears, respectively, without departing from the scope of the disclosure.

In the illustrated embodiment, the drive gears 512 may be coupled to or form part of each drive shaft 504a,b. Accordingly, rotation of the first drive shaft 504a, via rotation of the first capstan 502a and the intermeshed capstan drive and driven gears 506, 508, will cause the corresponding drive gear 512 to act on the first translating gear 510a. Similarly, rotation of the second drive shaft 504b, via rotation of the second capstan 502b and the intermeshed capstan drive and driven gears 506, 508, will cause the corresponding drive gear 512 to act on the second translating gear 510b.

In other embodiments, however, the first and second drive shafts 504a,b and the capstan drive and driven gears 506, 508 may be omitted. In such embodiments, the drive gears 512 may alternatively be coupled to or form part of the first and second capstans 502a,b. In such embodiments, rotation of the first capstan 502a may cause the corresponding drive gear 512 to directly act on the first translating gear 510a, and rotation of the second capstan 502b may cause the corresponding drive gear 512 to directly act on the second translating gear 510b. In either embodiment, rotation of the first and second capstans 502a,b, via actuation of the first and second drive inputs 406a,b of FIG. 4, respectively, will cause the corresponding drive gears 512 to act on the first and second translating gears 510a,b, respectively.

The shaft 202 may be axially fixed within the drive housing 208, but capable of rotation about the longitudinal axis $A_1$. The translating gears 510a,b may be rotationally fixed to the shaft 202, but capable of moving axially along a portion of the shaft 202 as acted upon by the corresponding drive gears 512. The first translating gear 510a may be directly or indirectly coupled to the first drive member 320a (FIG. 3) such that axial movement of the first translating gear 510a relative to the shaft 202 may correspondingly move the first drive member 320a in the same axial direction. Similarly, the second translating gear 510b may be directly or indirectly coupled to the second drive member 320b (see also FIG. 3) such that axial movement of the second translating gear 510b relative to the shaft 202 may correspondingly move the second drive member 320b in the same axial direction.

Since the translating gears 510a,b are each fixed rotationally to the shaft 202, acting on the translating gears 510a,b with the corresponding drive gears 512 will tend to urge the translating gears 510a,b to translate axially relative to the shaft 202, and thereby move the corresponding drive members 320a,b coupled thereto. Accordingly, articulation (pivoting) of the articulable joint 206 (FIG. 3) relative to the shaft 202 may be accomplished by driving one or both of the translating gears 510a,b with the corresponding drive gears 512, which correspondingly moves the associated drive members 320a,b.

In embodiments where the drive members 320a,b (FIG. 3) are rigid members (e.g., rods, shafts, bands, etc.), both of the translating gears 510a,b may be moved simultaneously to articulate the articulable joint 206 in the first or second directions 326a,b (FIG. 3). In such embodiments, the drive gears 512 may be driven in opposing directions, which results in the corresponding translating gears 510a,b moving axially relative to the shaft 202 in opposing directions (either toward or away from each other) and thereby articulating the articulable joint 206 in the first or second directions 326a,b. More specifically, articulating the articulable joint 206 in the first direction 326a may be accomplished by rotating the first capstan 502a in a first angular direction, and simultaneously rotating the second capstan 502b in a second angular direction opposite the first angular direction. Rotating the first capstan 502a in the first angular direction will cause the corresponding drive gear 512 to act on and drive the first translating gear 510a in the distal direction 324a and thereby simultaneously move the first drive member 320a (FIG. 3) distally 324a. In contrast, rotating the second capstan 502b in the second angular direction will cause the corresponding drive gear 512 to act on and drive the second translating gear 510b in the proximal direction 324b and thereby move the second drive member 320b (see also FIG. 3) proximally 324b.

Articulating the articulable joint 206 in the second direction 326b (FIG. 3) may be accomplished by reversing the rotation of the first and second capstans 502a,b. More specifically, rotating the first capstan 502a in the second angular direction will drive the first translating gear 510a in the proximal direction 324b and simultaneously move the first drive member 320a (FIG. 3) in the same direction. In contrast, rotating the second capstan 502b in the first angular direction will drive the second translating gear 510b in the distal direction 324a and thereby move the second drive member 320b (see also FIG. 3) in the same direction.

In embodiments where the drive members 320a,b are flexible or non-rigid members (e.g., a cable, a line, a cord, a wire, etc.), however, only one of the translating gears 510a,b may need to be moved to articulate the articulable joint 206 in the first or second directions 326a,b. In such embodiments, articulating the articulable joint 206 in the first direction 326a (FIG. 3) may be accomplished by rotating the second capstan 502b in the second angular direction, which will cause the corresponding drive gear 512 to act on and drive the second translating gear 510b in the proximal direction 324b and thereby pull the second drive member 320b (see also FIG. 3) proximally 324b. In some embodiments, as the articulable joint 206 rotates in the first direction 326a, the first capstan 502a may be actuated to maintain tension on the articulable joint 206. In contrast, articulating the articulable joint 206 in the second direction 326b (FIG. 3) may be accomplished by rotating the first capstan 502a in the first angular direction, which will cause the corresponding drive gear 512 to act on and drive the first translating gear 510a in the distal direction 324a and thereby pull the first drive member 320a (FIG. 3) distally 324a. In some embodiments, as the articulable joint 206 rotates in the second direction 326b, the second capstan 502b may be actuated to maintain tension on the articulable joint 206.

Since the translating gears 510a,b are each fixed rotationally to the shaft 202, if the drive gears 512 drive the corresponding translating gears 510a,b in the same direction, the shaft 202 may be urged to rotate about the longitudinal axis $A_1$. More specifically, rotating the first and second capstans 502a,b in the first angular direction will cause the corresponding drive gears 512 to act on the first and second translating gears 510a,b, respectively, in the same direction. As a result, the generated axial forces of each translating gear 510a,b may cancel out. Thus, instead of axial translation of the translating gears 510a,b, the canceled axial forces may urge the shaft 202 to rotate about the longitudinal axis $A_1$. To rotate the shaft 202 in the opposite direction, the first and second capstans 502a,b may simply be rotated in the second angular direction.

To rotate the shaft 202 about the longitudinal axis $A_1$, the rotational speed of the first and second capstans 502a,b may be substantially the same, thus equally canceling out the opposing axial forces caused by each translating gear 510a,b and instead converting that force into rotation. However, it may be possible to achieve compound motion if the rotational speed of the first and second capstans 502a,b is different. More specifically, to be able to rotate the shaft 202 about the longitudinal axis $A_1$ and simultaneously articulate the articulable joint 206 (FIG. 3) in the first or second directions 326a,b (FIG. 3), the rotational speed of one of the first and second capstans 502a,b may be increased or decreased relative to the rotational speed of the other. As a result, one of the axial forces generated by the translating gear 510a,b will be greater than the other, thus simultaneously driving the translating gears 510a,b in opposing directions (either toward or away from the other) while simultaneously causing rotation of the shaft 202.

Figure 6:
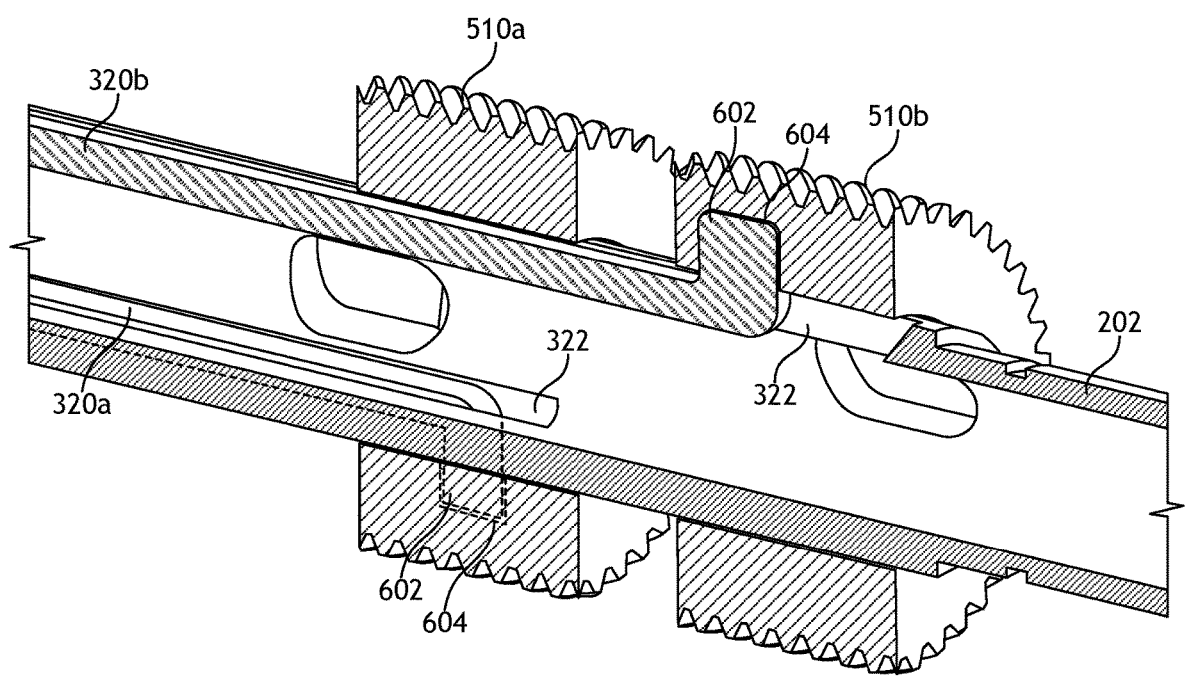
FIG. 6 is a cross-sectional side view of the translating gears of FIG. 5 positioned on the shaft, according to one or more embodiments.

FIG. 6 is a cross-sectional side view of the translating gears 510a,b positioned on the shaft 202, according to one or more embodiments. FIG. 6 also depicts the drive members 320a,b extending longitudinally within respective slots 322 defined in the shaft 202. As indicated above, the first translating gear 510a may be directly or indirectly coupled to the first drive member 320a, and the second translating gear 510b may be directly or indirectly coupled to the second drive member 320b.

In the illustrated embodiment, the first and second drive members 320a,b may be internally coupled to the translating gears 510a,b, respectively. More specifically, each drive member 320a,b may provide or otherwise define a projection or tab 602 extending laterally from the associated drive member 320a,b. The tabs 602 may be sized to be received within a slot 604 defined in the corresponding translating gears 510a,b. The slots 604 may be defined into the inner circumferential surface of each translating gear 510a,b, but could alternatively be defined at other locations, without departing from the scope of the disclosure. The tabs 602 may be permanently or removably secured within the corresponding slots 604 using, for example, an interference fit, an adhesive, welding, sonic (or ultrasonic) welding, one or more mechanical fasteners, a snap fit engagement, or any combination thereof.

Since the drive members 320a,b are positioned within the slots 322, mating the tabs 602 with the slots 604 effectively "keys" the translating gears 510a,b to the shaft 202 and thereby prevents the translating gears 510a,b from rotating relative to the shaft 202. Moreover, with the mated engagement between the tabs 602 and slots 604, axial movement of the translating gears 510a,b will correspondingly move the drive members 320a,b in the same axial direction within the associated slots 322.

Referring again to FIG. 5, in some embodiments, as illustrated, the shaft 202 may exhibit a generally circular cross-sectional shape. In such embodiments, the inner circumference of the translating gears 510a,b may also be generally circular to mate with the outer circumference of the shaft 202. In other embodiments, however, the shaft 202 need not be circular in cross-section, but may alternatively be polygonal (e.g., triangular, rectangular, etc.), oval, ovoid, or any combination thereof. In at least one embodiment, the shaft 202 may define or otherwise provide one or more planar surfaces 514 on its outer circumference. In such embodiments, corresponding flat or planar inner surfaces may be defined on the inner circumference of the translating gears 510a,b to help promote sliding engagement. This may also help prevent the translating gears 510a,b from rotating relative to the shaft 202.

At least one advantage provided by the presently disclosed embodiments is a reduction in part count. For conventional surgical tools, the drive housing typically requires three or more drive inputs to cause articulation of an articulable joint and rotation of a shaft. In contrast, the embodiments described herein require only the first and second drive inputs 406a,b (FIG. 4) to cause articulation of the articulable joint 206 (FIG. 3) and rotation of the shaft 202, which advantageously frees up another drive input for a different function. In some embodiments, as mentioned above, these movements may be done simultaneously, if desired. Another advantage provided by the presently disclosed embodiments is an increase in articulation output force since rotating the shaft 202 may now have the additive torque of an additional input, which effectively doubles the potential roll torque. Moreover, in some embodiments, articulation force may be increased by the mechanical advantage imparted by the drive inputs 408a,b to the helical gear arrangement of the translating gears 510a,b and the associated drive gears 512.

Embodiments disclosed herein include:

A. A surgical tool that includes a drive housing having a shaft extending distally therefrom, first and second drive members extending distally from the drive housing along the shaft, first and second translating gears rotationally fixed to the shaft within the drive housing and operatively coupled to the first and second drive members, respectively, and first and second drive gears rotatably mounted within the drive housing to act on the first and second translating gears, respectively, wherein rotating the first and second drive gears in opposite angular directions causes the first and second translating gears to move axially along the shaft in opposing directions and thereby move the first and second drive members, and wherein rotating the first and second drive gears in a same angular direction causes the first and second translating gears to rotate the shaft about a longitudinal axis.

B. A method of operating a surgical tool that includes positioning the surgical tool adjacent a patient for operation, the surgical tool including a drive housing having a shaft extending distally therefrom, first and second drive members extending distally from the drive housing along the shaft, first and second translating gears rotationally fixed to the shaft within the drive housing and operatively coupled to the first and second drive members, respectively, and first and second drive gears rotatably mounted within the drive housing to act on the first and second translating gears, respectively. The method further includes rotating the first and second drive gears in opposite angular directions and thereby causing the first and second translating gears to move axially along the shaft in opposing directions, moving the first and second drive members axially along the shaft as the first and second translating gears move, and rotating the first and second drive gears in a same angular direction and thereby causing the first and second translating gears to rotate the shaft about a longitudinal axis.

Each of embodiments A and B may have one or more of the following additional elements in any combination: Element 1: further comprising first and second capstans rotatably mounted within the drive housing, wherein rotation of the first and second capstans causes the first and second drive gears to rotate and act on the first and second translating gears, respectively. Element 2: further comprising first and second drive shafts rotatably mounted within the drive housing, wherein the first and second drive gears are coupled to the first and second drive shafts, respectively, first and second driven gears coupled to the first and second drive shafts, respectively, and first and second capstan drive gears coupled to the first and second capstans, respectively, and positioned to mesh with the first and second driven gears, respectively, wherein rotation of the first capstan controls rotation of the first drive shaft and the first drive gear, and wherein rotation of the second capstan controls rotation of the second drive shaft and the second drive gear. Element 3: wherein the first and second drive gears are coupled to the first and second capstans, respectively. Element 4: wherein the first and second drive members are positioned within corresponding slots defined longitudinally along all or a portion of the shaft. Element 5: further comprising an end effector operatively coupled to a distal end of the elongate shaft, and an articulable wrist that interposes the end effector and the elongate shaft, wherein the first and second drive members extend to the articulable wrist and rotating the first and second drive gears in the opposite angular directions causes the first and second drive members to articulate the articulable wrist. Element 6: wherein the first and second drive members are internally coupled to the first and second translating gears, respectively. Element 7: wherein the first drive member provides a first tab receivable within a first slot defined in an inner circumferential surface of the first translating gear, and wherein the second drive member provides a second tab receivable within a second slot defined in an inner circumferential surface of the second translating gear. Element 8: wherein the first and second drive members are selected from the group consisting of a rod, a shaft, a tube, a band, a cable, a line, a cord, a wire, a rope, a string, a twisted string, and any combination thereof. Element 9: wherein the shaft defines one or more planar surfaces on its outer circumference, and wherein one or more corresponding planar surfaces are defined on an inner circumference of one or both of the translating gears.

Element 10: wherein the surgical tool further includes first and second capstans rotatably mounted within the drive housing, the method further comprising rotating the first and second capstans and thereby rotating the first and second drive gears to act on the first and second translating gears, respectively. Element 11: wherein the surgical tool further includes first and second drive shafts rotatably mounted within the drive housing and the first and second drive gears are coupled to the first and second drive shafts, respectively, first and second driven gears coupled to the first and second drive shafts, respectively, and first and second capstan drive gears coupled to the first and second capstans, respectively, and positioned to mesh with the first and second driven gears, the method further comprising rotating the first capstan and thereby controlling rotation of the first drive shaft and the first drive gear, and rotating the second capstan and thereby controlling rotation of the second drive shaft and the second drive gear. Element 12: wherein positioning the surgical tool adjacent a patient for operation is preceded by mounting the drive housing to a tool driver of a robotic manipulator, wherein the drive housing includes first and second drive inputs matable with first and second actuators of the tool driver, and wherein the first and second capstans are coupled to the first and second drive inputs, respectively, and selectively actuating the first and second actuators based on user inputs and thereby rotating the first and second capstans, respectively. Element 13: wherein moving the first and second drive members axially along the shaft comprises slidably moving the first and second drive members within corresponding slots defined longitudinally along all or a portion of the shaft. Element 14: wherein the surgical tool further includes an end effector operatively coupled to a distal end of the elongate shaft, and an articulable wrist that interposes the end effector and the elongate shaft, the first and second drive members extending to the articulable wrist, and wherein moving the first and second drive members axially along the shaft further comprises articulating the articulable wrist as the first and second drive members move. Element 15: further comprising rotating the first and second drive gears in the same angular direction but at different speeds and thereby causing the first and second translating gears to move axially along the shaft in opposing directions and simultaneously causing the first and second translating gears to rotate the shaft about the longitudinal axis. Element 16: wherein the first and second drive members comprise flexible members, the method further comprises rotating the first drive gear and thereby causing the first translating gear to move axially along the shaft and simultaneously pull the first drive member proximally, articulating the articulable joint in a first direction as the first drive member is pulled proximally, actuating the second drive gear and thereby causing the second translating gear to place tension on the second drive member, and maintaining tension on the articulable joint in the first direction with the second drive member. Element 17: further comprising rotationally fixing the first and second translating gears to the shaft by internally coupling the first and second drive members to the first and second translating gears.

By way of non-limiting example, exemplary combinations applicable to A and B include: Element 1 with Element 2; Element 1 with Element 3; Element 6 with Element 7; Element 10 with Element 11; Element 10 with Element 12; Element 14 with Element 15; and Element 14 with Element 16.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

What is claimed is:

1. A surgical tool, comprising:
    a drive housing having a shaft extending distally therefrom;
    first and second drive members extending distally from the drive housing along the shaft;
    first and second translating gears rotationally fixed to the shaft within the drive housing and operatively coupled to the first and second drive members, respectively, the first and second translating gears being coaxially mounted to the shaft and separated from each other along an axis of the shaft; and
    first and second drive gears rotatably mounted within the drive housing, the first drive gear being arranged to act directly on the first translating gear, and the second drive gear being arranged to act directly on the second translating gear, wherein rotating the first and second drive gears in opposite angular directions causes the first and second translating gears to move axially along the shaft in opposing directions and thereby move the first and second drive members, and wherein rotating the first and second drive gears in a same angular direction causes the first and second translating gears to rotate the shaft about a longitudinal axis.

2. The surgical tool of claim 1, further comprising first and second capstans rotatably mounted within the drive housing, wherein rotation of the first and second capstans causes the first and second drive gears to rotate and act on the first and second translating gears, respectively.

3. The surgical tool of claim 2, further comprising:
first and second drive shafts rotatably mounted within the drive housing, wherein the first and second drive gears are coupled to the first and second drive shafts, respectively;
first and second driven gears coupled to the first and second drive shafts, respectively; and
first and second capstan drive gears coupled to the first and second capstans, respectively, and positioned to mesh with the first and second driven gears, respectively,
wherein rotation of the first capstan controls rotation of the first drive shaft and the first drive gear, and
wherein rotation of the second capstan controls rotation of the second drive shaft and the second drive gear.

4. The surgical tool of claim 2, wherein the first and second drive gears are coupled to the first and second capstans, respectively.

5. The surgical tool of claim 1, wherein the first and second drive members are positioned within corresponding slots defined longitudinally along all or a portion of the shaft.

6. The surgical tool of claim 1, further comprising:
an end effector operatively coupled to a distal end of the elongate shaft; and
an articulable wrist that interposes the end effector and the elongate shaft,
wherein the first and second drive members extend to the articulable wrist and rotating the first and second drive gears in the opposite angular directions causes the first and second drive members to articulate the articulable wrist.

7. The surgical tool of claim 1, wherein the first and second drive members are internally coupled to the first and second translating gears, respectively.

8. The surgical tool of claim 7, wherein the first drive member provides a first tab receivable within a first slot defined in an inner circumferential surface of the first translating gear, and wherein the second drive member provides a second tab receivable within a second slot defined in an inner circumferential surface of the second translating gear.

9. The surgical tool of claim 1, wherein the first and second drive members are selected from the group consisting of a rod, a shaft, a tube, a band, a cable, a line, a cord, a wire, a rope, a string, a twisted string, and any combination thereof.

10. The surgical tool of claim 1, wherein the shaft defines one or more planar surfaces on its outer circumference, and wherein one or more corresponding planar surfaces are defined on an inner circumference of one or both of the translating gears.

11. A method of operating a surgical tool, comprising:
positioning the surgical tool adjacent a patient for operation, the surgical tool including:
a drive housing having a shaft extending distally therefrom;
first and second drive members extending distally from the drive housing along the shaft;
first and second translating gears rotationally fixed to the shaft within the drive housing and operatively coupled to the first and second drive members, respectively, the first and second translating gears being coaxially mounted to the shaft and separated from each other along an axis of the shaft; and
first and second drive gears rotatably mounted within the drive housing, the first drive gear being arranged to act directly on the first translating gear, and the second drive gear being arranged to act directly on the second translating gear,
rotating the first and second drive gears in opposite angular directions and thereby causing the first and second translating gears to move axially along the shaft in opposing directions;
moving the first and second drive members axially along the shaft as the first and second translating gears move; and
rotating the first and second drive gears in a same angular direction and thereby causing the first and second translating gears to rotate the shaft about a longitudinal axis.

12. The method of claim 11, wherein the surgical tool further includes first and second capstans rotatably mounted within the drive housing, the method further comprising rotating the first and second capstans and thereby rotating the first and second drive gears to act on the first and second translating gears, respectively.

13. The method of claim 12, wherein the surgical tool further includes first and second drive shafts rotatably mounted within the drive housing and the first and second drive gears are coupled to the first and second drive shafts, respectively, first and second driven gears coupled to the first and second drive shafts, respectively, and first and second capstan drive gears coupled to the first and second capstans, respectively, and positioned to mesh with the first and second driven gears, the method further comprising:
rotating the first capstan and thereby controlling rotation of the first drive shaft and the first drive gear; and
rotating the second capstan and thereby controlling rotation of the second drive shaft and the second drive gear.

14. The method of claim 12, wherein positioning the surgical tool adjacent a patient for operation is preceded by:
mounting the drive housing to a tool driver of a robotic manipulator, wherein the drive housing includes first and second drive inputs matable with first and second actuators of the tool driver, and wherein the first and second capstans are coupled to the first and second drive inputs, respectively; and selectively actuating the first and second actuators based on user inputs and thereby rotating the first and second capstans, respectively.

15. The method of claim 11, wherein moving the first and second drive members axially along the shaft comprises slidably moving the first and second drive members within corresponding slots defined longitudinally along all or a portion of the shaft.

16. The method of claim 11, wherein the surgical tool further includes an end effector operatively coupled to a distal end of the elongate shaft, and an articulable wrist that interposes the end effector and the elongate shaft, the first and second drive members extending to the articulable wrist, and wherein moving the first and second drive members axially along the shaft further comprises articulating the articulable wrist as the first and second drive members move.

17. The method of claim 16, further comprising rotating the first and second drive gears in the same angular direction but at different speeds and thereby causing the first and second translating gears to move axially along the shaft in opposing directions and simultaneously causing the first and second translating gears to rotate the shaft about the longitudinal axis.

18. The method of claim 16, wherein the first and second drive members comprise flexible members, the method further comprises:

rotating the first drive gear and thereby causing the first translating gear to move axially along the shaft and simultaneously pull the first drive member proximally;

articulating the articulable wrist in a first direction as the first drive member is pulled proximally;

actuating the second drive gear and thereby causing the second translating gear to place tension on the second drive member; and maintaining tension on the articulable wrist in the first direction with the second drive member.

19. The method of claim 11, further comprising rotationally fixing the first and second translating gears to the shaft by internally coupling the first and second drive members to the first and second translating gears.

* * * * *